United States Patent [19]
Pernot

[11] Patent Number: 5,555,976
[45] Date of Patent: Sep. 17, 1996

[54] PACKAGING FOR A SURGICAL SUTURE

[75] Inventor: Pascal C. R. Pernot, Chartres, France

[73] Assignee: Ethicon, Inc., Somerville, N.J.

[21] Appl. No.: 408,503

[22] Filed: Mar. 22, 1995

[51] Int. Cl.$^6$ .................................................. A61B 17/06
[52] U.S. Cl. ........................ 206/63.3; 206/380; 206/227
[58] Field of Search ................................ 206/63.3, 380, 206/382, 227, 495

[56] References Cited

U.S. PATENT DOCUMENTS

| | | | |
|---|---|---|---|
| 4,249,656 | 2/1981 | Cerwin et al. | 206/63.3 |
| 4,284,194 | 8/1981 | Flatau | 206/63.3 |
| 4,369,880 | 1/1983 | Giggey et al. | 206/380 |
| 4,412,614 | 11/1983 | Ivanov et al. | 206/63.3 |
| 4,555,016 | 11/1985 | Aday et al. | 206/63.3 |
| 5,101,968 | 4/1992 | Hendersen et al. | 206/227 |
| 5,390,782 | 2/1995 | Sinn | 206/63.3 |
| 5,425,445 | 6/1995 | Brown et al. | 206/63.3 |

*Primary Examiner*—David T. Fidei
*Attorney, Agent, or Firm*—Emil R. Skula

[57] ABSTRACT

The present invention relates to a support-wrapping for a surgical suture including a pivotally-hinged flap having the needle of the suture fixed thereto. The invention also provides packaging for a surgical suture and that includes a support-wrapping of the above-specified type.

6 Claims, 2 Drawing Sheets

PACKAGING FOR A SURGICAL SUTURE

The present invention relates to the field of packaging for surgical sutures.

BACKGROUND OF THE INVENTION

Numerous types of packaging for surgical sutures have already been proposed.

For example, packaging has been proposed that comprises cradles of plastics material designed to be placed in a cardboard sheath prior to being inserted in a sterile outer envelope.

Packaging for surgical sutures has also been proposed comprising simple card wrapping designed to be placed inside a sterile outer envelope.

OBJECT AND SUMMARY OF THE INVENTION

The object of the present invention is to improve previously-known packaging for surgical sutures.

In particular, an important object of the present invention is to propose novel packaging for a surgical suture designed to facilitate access to the needle of the suture.

In the context of the present invention, this object is achieved by support-wrapping for a surgical suture comprising cuts and folds in a card blank that is made up of three elements that are connected together in pairs by respective fold lines, the thread of the suture being essentially situated between two adjacent elements of the support-wrapping, and the wrapping further including a pivotally-hinged opening flap on the third element with the needle of the suture being fixed to said opening flap at a distance from its hinge axis and also from the zone where the thread emerges from between the two first-mentioned elements, such that on opening the support-wrapping, the pivoting of the opening flap causes the needle to be moved away from the basic structure of the support-Wrapping, thereby facilitating subsequent grasping of the needle.

Advantageously, according to another characteristic of the invention, the means for fixing the needle to the opening flap are formed by a block of foam so adapted that when the opening flap pivots, not only does the needle move away from the base structure of the support-wrapping, but it also pivots inside the block of foam. This pivoting makes it possible for the needle to be released from the opening flap, thereby enabling it to be grasped properly.

BRIEF DESCRIPTION OF THE DRAWINGS

Other characteristics, objects, and advantages of the present invention appear on reading the following detailed description with reference to the accompanying drawings that are given by way of non-limiting example, and in which.

MORE DETAILED DESCRIPTION

Figure 1:
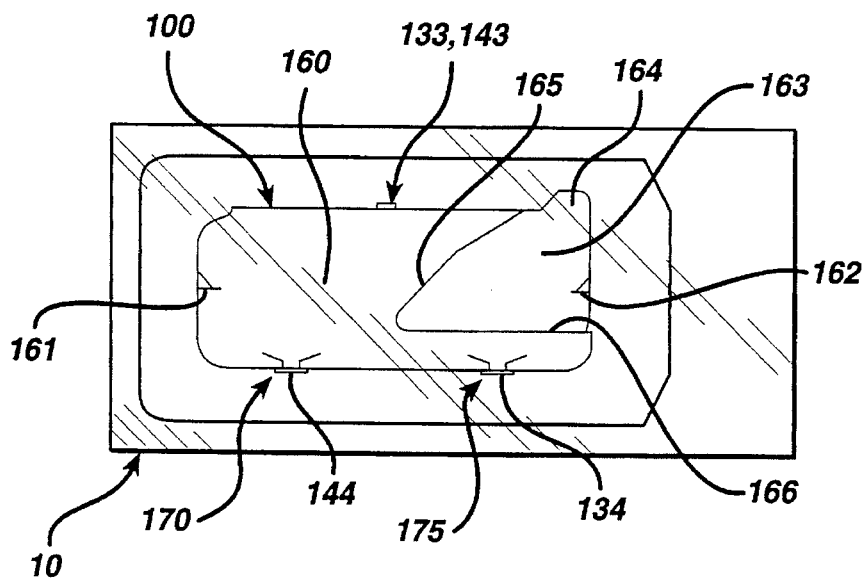
FIG. 1 is a diagrammatic plan view of packaging for a surgical suture in accordance with the present invention.

As can be seen in accompanying FIG. 1, the packaging for a surgical suture of the present invention essentially comprises a support-wrapping 100 placed in an outer envelope 10.

The outer envelope 10 is conventional per se and is therefore not described in detail below.

It is nevertheless recalled that the outer envelope 10 is sterile. It may advantageously be made up of two sheets that are connected together at their peripheries and that are suitable for peeling apart, thereby forming a pocket that is closed and suitable for containing the support-wrapping 100. By way of non-limiting example, the outer envelope 10 may be made up of a sheet that is paper-based plus a second sheet that is made of an optically transparent plastics material.

In the accompanying drawings, the thread of the suture is reference 20, while its needle is referenced 22.

The structure of the support-wrapping 100 of the present invention is now described in detail.

Figure 4:
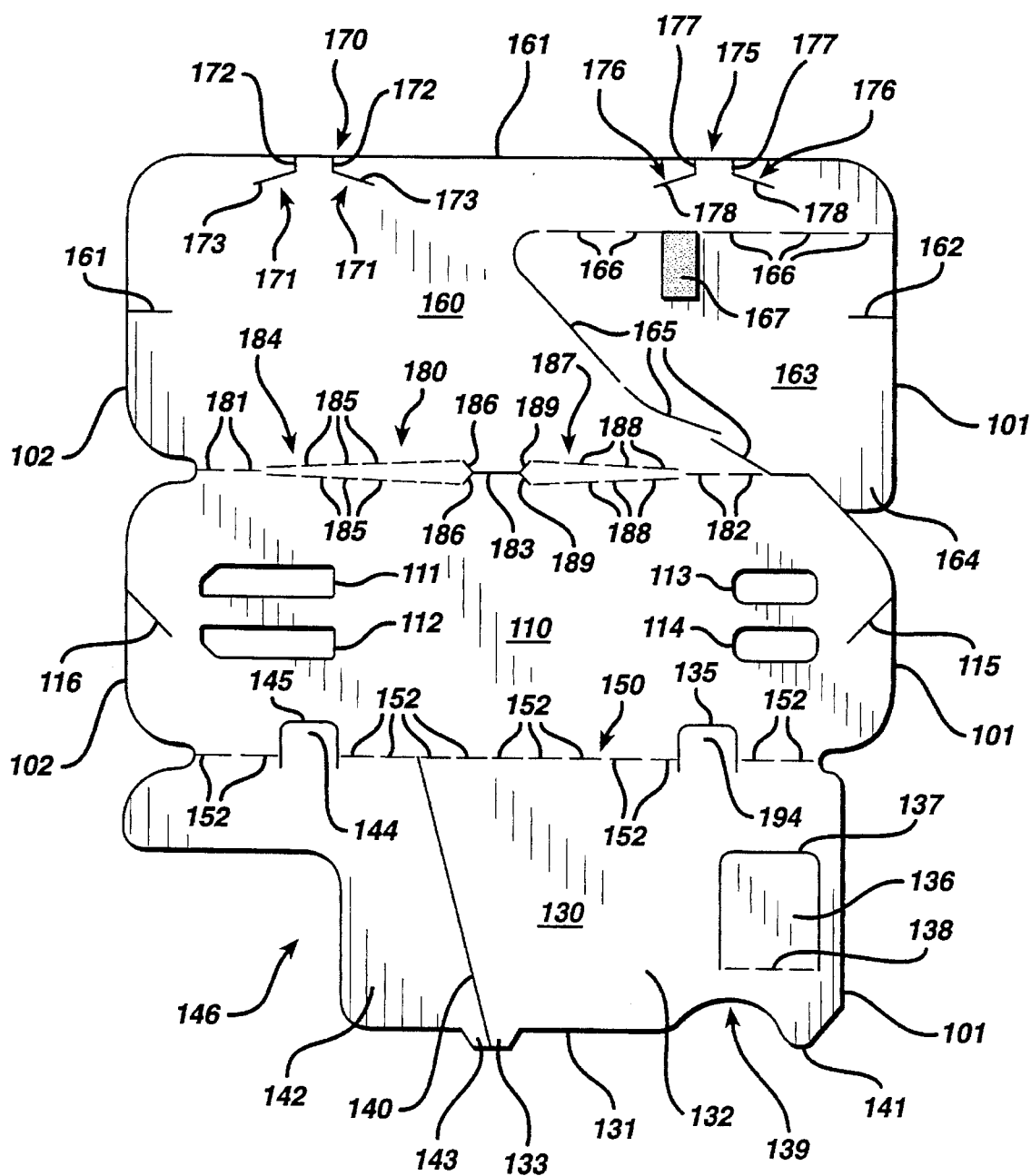
FIG. 4 is a plan view of the card blank used for making support-wrapping of the present invention.

The support-structure 100 is made by cutting and folding a single card blank as shown in FIG. 4.

As can be seen on examining FIG. 4, the card blank is initially generally rectangular in overall outline. More precisely, three elements 110, 130 and 160 are defined in the blank by folding. These elements 110, 130, and 160 are connected together in pairs by hinge lines 150 and 180 which are described in greater detail below.

To simplify the detailed description below, the element 110 is referred to as the "middle" element, the element 130 is referred to as the "inner" element (because it is placed inside the wrapping after the wrapping has been closed), and the element 160 is referred to as the "outer" element (because it is placed on the outside of the wrapping after the wrapping has been closed).

In addition, the terms "inner longitudinal edge" and "outer longitudinal edge" are used respectively for the edges of the blank that are referenced 131 and 161 in FIG. 4, and the term "end edges" is used for the edges referenced 101 and 102 in FIG. 4. The end edges 101 and 102 are orthogonal to the longitudinal edges 131 and 161.

The above-specified fold lines 150 and 180 extend generally parallel to the longitudinal edges 131 and 161 and perpendicularly to the end edges 101 and 102.

FIG. 4 shows the inside face of the blank or wrapping.

The fold line 150 interconnecting the middle element and the inner element 130 includes a series of cuts constituted by non-touching rectilinear segments parallel to the longitudinal edges 131 and 161.

The segments 152 thus extend generally between the end edges 101 and 102.

The segments 152 are all in alignment.

The second fold line 180 is formed between the middle element 110 and the outer element 160.

This fold line 180 is made up of:

two non-touching rectilinear cut segments 181 that are in alignment and adjacent to end edge 102;

two non-touching rectilinear cut segments 182 that are aligned with each other and also with the segments 181, and that are adjacent to the other end edge 101;

a central rectilinear cut segment 183 that is in alignment with above-mentioned segments 181 and 182; and two symmetrical sets of cuts 184 and 187, one set being situated between the segments 181 and the central segment 183, and the other set being situated between the central segment 183 and the segments 182.

Each of the two sets 184 and 187 comprises two series of cuts respectively referenced 185 and 188. Each series of cuts 185 or 188 is made up of rectilinear segments in alignment. In addition, the two series of cuts constituting each set, i.e. the series 185 in the set 184 and the series 188 in the set 187, diverge towards the central segment 183.

Furthermore, each of the sets 184 and 187 has two additional segments respectively referenced 186 and 189 that are V-shaped. Thus, the additional segments 186 and converge on the central segment 183 and they connect respective ends of said central segment 183 to the ends of the above-mentioned series of segments 185 and 188.

The fold line 180 thus defined by cut segments 181 to 189 has the purpose of imparting volume to the support-wrapping 100. The person skilled in the art will readily understand that after folding, the thickness of the support-wrapping 100 corresponds to the spacing between the two series of cut segments 185 and 188, respectively. In other words, the thickness of the support-wrapping increases progressively, starting from the end edges 101 and 102 and going towards the center of the wrapping.

The structure of the middle element 110 is now described.

This middle element 110 has two pairs of through windows 111, 112, 113, and 114. Each window 111, 112, 113, and 114 is generally in the form of an elongate rectangle with rounded corners. Each pair of windows 111 & 112 and 113 & 114 is symmetrical about a midplane orthogonal to the element 110 and parallel to the fold lines 150 and 180.

The first pair of windows 111 & 112 is situated close to end edge 102, while the second pair of windows 113 & 114 is situated close to the second end edge 101. The windows 111, 112, 113, and 114 are elongate parallel to the fold lines 150 and 180.

The purpose of the windows 111, 112, 113, and 114 is to pass pegs that serve in conventional manner as temporary supports for suture threads while they are being coiled.

The middle element 110 also includes straight cuts 115 and 116 in its end edges 101 and 102 respectively.

The cuts 115 and 116 slope relative to the end edges 101 and 102, advantageously at 45°.

The cuts 115 and 116 converge towards the fold line 150 on going towards the inside of the card blank 100.

The cuts 115 and 116 open out into the end edges 101 and 102 substantially in the middles thereof in the middle element 110.

More precisely, the midpoint of each of the cuts 115 and 116 is preferably situated level with the middle of each of the end edges 101 and 102 of the middle element 110, such that the cuts 115 and 116 open out between the midpoints of the end edges 101 and 102, and the fold line 180.

The structure of the inner element 130 is now described.

The inner element 130 is preferably split into two portions 132 and 142 by a cut 140.

The cut 140 is advantageously rectilinear. It connects the fold line 150 to the longitudinal edge 131. More precisely, the rectilinear cut line 140 advantageously slopes relative to the fold line 150 and to the longitudinal edge 131, i.e. it is not perpendicular thereto.

The cut 140 converges towards the end edge 101 as it goes towards the longitudinal edge 131.

The cut 140 opens out in the longitudinal edge 131 substantially halfway along the longitudinal edge 131.

The inner element 130 has two projecting tongues 133 and 134 which project beyond the longitudinal edge 131 on respective sides of the cut 140, i.e. on the two portions 132 and 142 respectively.

The width of the inner element 130 as measured parallel to the end edges 101 and 102 is equal to the corresponding width of the middle element 110, so the purpose of the projecting tongues 133 and 143 is to penetrate into the above-described central cut 183 so as to enable the inner element 130 and the middle element 110 to be held together face-to-face in a closed position.

Level with the fold line 150, each of the two portions 132 and 142 of the inner element 130 is provided with a respective projecting lug 134, 144. The lugs 134 and 144 are preferably rectilinear in outline. They are defined by respective U-shaped cuts 135 and 145. These lugs 134 and 144 thus extend into the middle element 110, i.e. they extend beyond the fold line 150. The purpose of the lugs 134 and 144 is to co-operate with complementary cuts on the longitudinal edge 161 of the outer element 160 so as to lock the support-wrapping 100 in its closed position.

The first portion 132 of the inner element 130 adjacent to the end edge 101 further includes a pivotally hinged flap 136. The flap 136 is defined by a U-shaped cut 137. It is hinged to the portion 132 by means of a fold line formed by a series of non-touching rectilinear cut segments 138 in alignment. The segments 138 run between the ends of the U-shaped cut 137.

The flap 136 is positioned on the portion 132 in such a manner as to be situated facing the windows 113 and 114 of the middle element 110 when the inner element is placed against the middle element 110 by folding about fold line 150. The purpose of the flap 136 is to prevent any interference between the portion 132 of the inner element 130 and the pegs placed in the windows 113 and 14, while still allowing the wound thread to be held in place.

Thus, as explained below, to assemble the support-wrapping, the inner element 130 is folded against the middle element 110 prior to the pegs that are placed in the windows 113 and 114 being withdrawn.

Preferably, the portion 132 is provided on its longitudinal edge 131 and in the vicinity of the end edge 101 with a bight 139 set back towards the inside of the portion 131, and followed by a tooth 141 projecting beyond the longitudinal edge 131, which tooth 141 is adjacent to the end edge 101.

As will be understood on examining the accompanying figures, this bight 139 and tooth 141 serve to hold the thread in its portion adjacent to the needle 22, while still leaving the thread with a certain amount of freedom while the wrapping is being opened.

It will be observed that the end edge 101 of the inner element 130 is set back from the cut 115 formed in the middle element 110 and opening out in the corresponding end edge 101. In other words, the length of the inner element 130 taken parallel to the longitudinal edge 131 is shorter than the corresponding length of the middle element 110.

The second portion 142 is provided with a large cutout 146 which connects the end edge 102 to the longitudinal edge 131. This cutout 146 is located facing the windows 111 and 112 formed in the middle element 110 so as to act in a manner comparable to the flap 136 to allow the portion 142 to be folded against the middle element 110 without said portion 142 interfering with the pegs placed in the windows 111 and 112.

The structure of the outer element 160 as shown in the figures is now described.

The outer element 160 has two rectilinear cuts 161 and 162 opening out respectively into the end edges 101 and 102. The cuts 161 and 162 extend perpendicularly to said end edges 101 and 102, and they are located halfway across the width of the outer element 160. The purpose of the cuts 161 and 162 is to receive the two triangular shapes defined by the cuts 115 and 116 in the middle element 110, as can be seen in particular in FIG. 1, thereby keeping the wrapping closed when it is in its closed position.

The longitudinal edge 161 of the outer element 160 on its side opposite from the fold line 180 has cuts designed to co-operate with the lugs 134, 144 of the inner element 130. More precisely, two sets of cuts 170, 175 are thus provided, each set being designed to correspond with a respective lug 134 or 144.

Each set 170, 175 comprises two cuts 171, 176 disposed symmetrically about a plane orthogonal to the longitudinal edge 161.

More precisely, each cut 171, 176 comprises a first segment 172, 177 and a second segment 173, 178.

Each first segment 172, 177 is rectilinear and opens out into the longitudinal edge 161 perpendicularly thereto. Each second segment 173, 178 extends the corresponding first segment 172, 177 towards the inside of the outer element 160. Each rectilinear second segment 173, 178 slopes at a few degrees relative to the longitudinal edge 161. It diverges away from said longitudinal edge 161 on going towards its own free end. In addition, the second segments 173, 178 of each set 170, 175 diverge mutually, going towards their own free ends.

The distance between each pair of first segments 172 or 177 is less than the width of each of the lugs 134, 144 as measured parallel to the fold lines 150, 180. However, the distance between the ends of the corresponding pairs of second segments 173 and 178 is greater than the above-specified width of the lugs 134, 144.

The outer element 160 also includes a flap 163. The flap 163 has a tab 164 projecting beyond the fold line 180. The tab 164 is adjacent to end edge 101.

The purpose of the tab 164 is to facilitate grasping the flap 163 for the purpose of separating it in part from the remainder of the outer element 160, with the flap 163 pivoting in a manner that is described below.

The flap 163 is defined in part by a broken line formed by various cut segments 165.

The flap 163 is hinged to the outer element 160 via a line made up of various non-touching rectilinear cut segments 166 that are in alignment. These segments 166 open out to the end edge 101 close to the longitudinal edge 161. The segments 166 extend parallel to said longitudinal edge 161.

The segments 165 which define the flap 163 thus connect the inner end of the line of cut segments 166 to the hinge line 180 close to the end edge 101.

The flap 163 is also provided with means for holding the needle 22 of the suture in removable manner. These holding means are preferably formed by a block of foam or the equivalent given reference 167 in accompanying FIG. 4. The block of foam 167 which may be rectilinear in outline is stuck onto the flap 163 preferably substantially halfway along it, close to the pivoting hinge line formed by the cut segments 166.

It should be observed that the corners of the three elements 110, 130, and 160 are preferably rounded.

To assemble a suture support-wrapping 100 of the present invention, the procedure is essentially as follows.

After the various structures as described above have been cut, the blank 100 is presented in the plane state on a conventional coiling machine. Thread support pegs are thus positioned in the windows 111, 112, 113, and 114.

The suture thread is then coiled in conventional manner on the above-mentioned pegs. The suture thread is advantageously coiled in a figure-eight configuration in conventional manner so as to prevent any untimely tangling of the thread in use.

After coiling, the two portions 132 and 142 of the inner element 130 can be folded successively against the middle element 110 without interfering with the above-mentioned pegs. The suture thread is thus properly held in place between the middle element 110 and the inner element 130. The above-specified pegs can then be withdrawn.

The portions 132 and 142 are locked to the middle element 110 by inserting their respective projecting tongues 133, 143 into the central cut 183. The suture needle 22 is pushed into the block of foam 167. The outer element 160 can then be folded in turn against the inner element 130.

The outer element 160 is held in place firstly by engaging the lugs 134 and 144 in the two sets of cuts 175 and 170, and secondly by engaging the shapes defined by the cuts 115 and 116 in the middle element 110 in the cuts 162 and 161.

Figure 2:
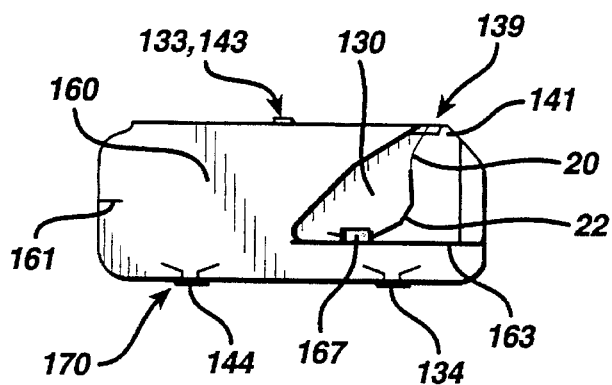
FIG. 2 is a plan view of the support-wrapping of the present invention after the pivotally-hinged flap has been opened.
Figure 3:
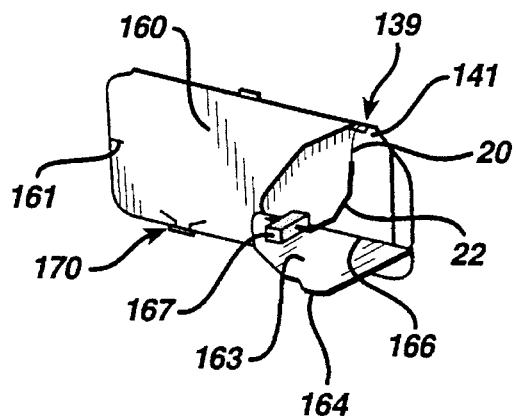
FIG. 3 is a perspective view of the same support-wrapping, after the above-specified pivotally-hinged flap has been opened.

In use, it suffices to take hold of the tab 164 and use it to pull back the flap 163 so as to break the bridges previously separating the segments 165, thereby enabling the flap 163 to pivot about the hinge line defined by the segments 166, as can be seen in FIGS. 2 and 3.

The user can then easily gain full access to the needle 22.

It should be observed that according to an important characteristic of the invention, since the needle 22 is preferably initially engaged in the block of foam 167 at a distance from the hinge link 166, the fact of pivoting the flap 163 relative to the remainder of the outer element 160 has the effect of moving the needle away from the supporting wrapping, as can be seen in FIG. 3. This offset of the needle 22 facilitates subsequent grasping thereof, e.g. by means of a forceps system.

In addition, the flap 163 can be used to guide the forceps system so as to further facilitate grasping the needle 22.

The support-wrapping of the present invention is particularly simple, reliable, and easy to use, and it ensures that the needle 22 is firmly held prior to use.

Where appropriate, the support-wrapping 100, which is made of card, may be printed on its outer face, to identify the kind of thread 20 or needle 22, and also the dimensions thereof.

For this purpose, the outer envelope 10 preferably includes at least one optically transparent sheet so as to enable the information printed on the support-wrapping 100 to be read prior to the envelope 10 being opened.

Naturally, the present invention is not limited to the particular embodiment described, but extends to any variant coming within the spirit thereof.

Thus, in one variant, the support-wrapping 100 may received sutures fitted with two or more needles 22 secured to a single thread 20 or to a plurality of threads. Under such circumstances, it is advantageous to provide two or more blocks of foam on the outer element 160. These two blocks of foam may be fixed to the pivotally-hinged flap 163 in such a manner that opening the flap causes all of the various needles 22 to be offset simultaneously.

In another variant, it is possible to provide a block of foam 167 that receives a first needle 22 which is fixed on the flap 163, together with at least one second block of foam that is designed to receive the other needle(s) 22 and that is stuck to the inside face of the element 160, but not on the flap 163.

Under such circumstances, the additional block(s) of foam may optionally be placed on additional flap(s) similar to the flap 163 and pivotally hinged to the outer element 160 so as to enable the other needle(s) to be moved in turn away from the supporting wrapping on opening the above-mentioned additional flap(s).

As can be seen on examining FIG. 3, when the hinged flap 163 is in its open position, it may be used as a prop for the support-wrapping, enabling the wrapping to stand up in a generally vertical position.

It will also be observed that, in accordance with the invention, the suture thread 20 is situated essentially between the middle element 110 and the inner element 130, while the needle 22 is situated between the inner element 130 and the outer element 160. As a result, the inner element 130 serves to separate the needle 22 from the thread 20, thereby avoiding any deterioration of the thread 20 during storage.

I claim:

1. A support-wrapping for a surgical suture and needle, comprising:

cuts and folds in a card blank that is made up of three elements that are connected together in pairs by respective fold lines, the thread of the suture being essentially situated between two adjacent elements of the support-wrapping, and the wrapping further including a pivotally-hinged opening flap having a hinge axis on the third element with the needle of the suture being fixed to said opening flap at a distance from its hinge axis and also from the zone where the thread emerges from between the two first-mentioned elements, such that on opening the support-wrapping, the pivoting of the opening flap causes the needle to be moved away from the basic structure of the support-wrapping, thereby facilitating subsequent grasping of the needle;

means for fixing the needle on the pivotally-hinged flap comprising a block of foam;

at least one fold line to give volume to the support-wrapping including two series of cuts that are substantially adjacent and parallel;

a middle element between two fold lines having windows designed to receive pegs that are used as supports for the suture while it is being coiled;

an element that has cuts opening out into its end edges and that slope relative thereto;

an element that is split into two portions by a line of cuts and wherein both of the two portions comprise a respective projecting tongue on respective opposite sides of the line of cut, which projecting tongues are designed to penetrate into a complementary cut so as to lock the support-wrapping;

at least one element having at least one projecting lug designed to cooperate with a complementary set of cuts in order to lock the support-wrapping in a closed position;

at least one element that has a hinged flap which is situated, after folding, so as to overlie windows formed in another element of the support-wrapping;

at least one element having a cutout situated to overlie windows placed in another element after the support-wrapping structure has been folded;

at least one element having cuts that open out in the end edges of the wrapping and that are designed to cooperate with complementary cuts formed in another element; and, at least one set of cuts designed to cooperate with a projecting lug formed on an adjacent element wherein each set of cuts comprises two cuts each having a first segment that opens out into the longitudinal edge of the support-wrapping that is substantially orthogonal thereto, followed by a second segment diverging towards the inside of the wrapping.

2. A support-wrapping according to claim 1, wherein the pivotally hinged flap includes a projecting tab for grasping purposes.

3. A support-wrapping according to claim 1, including information printed on its outside surface.

4. A support-wrapping according to claim 1, including at least two needles.

5. A support-wrapping according to claim 4, including at least two foam blocks designed to receive respective needles.

6. Packaging for a surgical suture, comprising a sterile outer envelope receiving a support-wrapping according to claim 1.

* * * * *